United States Patent [19]  [11]  4,038,316
Duranleau et al.  [45]  July 26, 1977

[54] PREPARATION OF ACYLHYDROXIMYL HALIDES

[75] Inventors: Roger G. Duranleau, Ardonia; John M. Larkin, Wappingers Falls, both of N.Y.

[73] Assignee: Texaco Inc., New York, N.Y.

[21] Appl. No.: 638,408

[22] Filed: Dec. 8, 1975

Related U.S. Application Data

[62] Division of Ser. No. 532,421, Dec. 12, 1974, Pat. No. 3,960,953.

[51] Int. Cl.$^2$ ............................................. C07C 131/00
[52] U.S. Cl. ................................................ 260/566 A
[58] Field of Search ..................................... 260/566 A

[56] References Cited
PUBLICATIONS

Hurd et al., J. Org. Chem., vol. 20, pp. 927–936, (1955).

*Primary Examiner*—Gerald A. Schwartz
*Attorney, Agent, or Firm*—Thomas H. Whaley; Carl G. Ries; George J. Darsa

[57] ABSTRACT

Novel acylhydroximyl halides are provided and prepared by contacting a nitroalkanone with a halogen acid in the presence of an organic acid or alcohol.

12 Claims, No Drawings

PREPARATION OF ACYLHYDROXIMYL HALIDES

This is a division of application Ser. No. 532,421 filed Dec. 12, 1974, now U.S. Pat. No. 3,960,953 issued June 1, 1976.

BACKGROUND OF THE INVENTION

This invention relates to novel acylhydroximyl halides and to a method of preparing acylhydroximyl halides from nitroketones.

Heretofore, only certain acylhydroximyl halides, namely the chlorides, have been disclosed and prepared by reacting a low molecular weight 1-nitro-2-alkanone, that is nitroketones having three or four carbons such as nitroacetone or 1-nitro-2-butanone, in concentrated hydrochloric acid at ambient temperatures. While this earlier method provided acceptable yields of the desired chloride product, extended reaction times of twenty or more hours were reported in providing the material. Further, the earlier method is applicable only to the preparation of low molecular weight acylhydroximyl chlorides inasmuch as we have found that higher molecular weight nitroalkanones that is, those having at least five carbons and particularly those of seven carbons and higher either form poor yields of the product or do not react with hydrochloric acid.

It is therefore an object of this invention to provide novel acylhydroximyl halides and to a method for their preparation.

Another object of this invention is to provide a method for the preparation of acylhydroximyl halides good yields over shortened reaction times.

Yet another object of this invention is to provide a method applicable to the preparation of acylhydroximyl halides from low and higher molecular weight nitroalkanones.

Other objects and advantages will become apparent from the following detailed description and examples.

SUMMARY OF THE INVENTION

Broadly, this invention contemplates a method of preparing acylhydroximyl halides which comprises contacting a nitroketone with a halogen acid in the presence of a polar protic organic solvent.

Pursuant to this invention the contemplated acylhydroximyl halides are prepared from 1-nitro-2-alkanones corresponding to the formula:

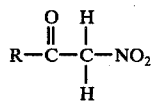

where R is an alkyl group having from 1 to 50 carbon atoms, suitably from 3 to 40 carbons and preferably 5 to 30 carbons. Illustrative of the starting materials we mention 1-nitro-2-propanone, 1-nitro-2-butanone, 1-nitro-2-pentanone, 1-nitro-2-hexanone, 1-nitro-2-heptanone, 1-nitro-2-octanone, 1-nitro-2-decanone, 1-nitro-2-dodecanone, 1-nitro-2-pentadecanone, 1-nitro-2-hexadecanone, 1-nitro-2-heptadecanone, 1-nitro-2-eicosanone, and 1-nitro-2-heneicosanone. The vicinal nitroketones contemplated as reactants herein can be prepared by methods known to the art, as for example the procedure described in U.S. Pat. No. 3,415,856. Essentially, the procedure involves a nitrooxidation reaction by contacting a 1-olefin with dinitrogen tetroxide and oxygen to form a peroxy intermediate and thereafter contacting the peroxy compound with a denitrating agent. Internal nitroketones, that is, nitroketones prepared from other than 1-olefins or from cyclic alkenes and where the nitro group is on other than a terminal carbon or where an alphanitrocycloalkanone is formed, do not react in the instant method to produce for example any acylhydroximyl chloride.

More specifically, the process of this invention comprises contacting a 1-nitro-2-alkanone as hereinabove defined or mixtures thereof with a halogen acid in the presence of a polar protic organic solvent at a temperature of from about 50° C. to 105° C., preferably from 70° to 100° C. Temperatures below about 50° C. cause slow reaction and temperatures greater than about 105° C. cause a substantial reduction in the desired product.

In accordance with the inventive process a nitroketone of the formula above is contacted with a halogen acid, including hydrochloric acid, hydrobromic acid, hydroiodic acid or hydrofluoric acid, in the presence of the solvent in a mole ratio of nitroketone to halogen acid to solvent of between about 1:1:1 and 1:30:100, preferably between about 1:2:4 and 1:10:40. The mole ratios mentioned above permit the nitroketone and the halogen acid to be at least partially soluble in the solvent at the reaction temperature. By insuring at least partial solubility of the nitroketone and halogen acid in the solvent, reaction times are shortened and improved yields of acylhydroximyl halides are realized. Moreover, essentially complete conversion of the nitroketone to the desired product results and the product is easily recovered from the reaction mixture. While dilute or concentrated halogen acids can be employed, the use of concentrated acids is preferred. Further, the amount of water in the dilute acids, particularly when the higher mole ratio of halogen acid are employed, should be below tht amount which causes the nitroketone to become insoluble in the solvent. The amount of water causing the loss of solubility of the nitroketone in the solvent will vary depending upon the particular solvent employed and the molecular weight of the nitroketone and the same can be easily determined by experimention. In general, employing the mole ratios of materials set out above, provides a system where the nitroketone is soluble in the solvent.

The polar protic organic solvent contemplated herein and employed in our method can be a carboxylic acid or alcohol having from 2 to 16 carbons such as acetic acid, propionic acid, butanoic acid, isobutanoic acid, pentanoic acid, hexanoic acid, octanoic acid, decanoic acid, undecanoic acid, dodecanoic acid, hexadecanoic acid, ethanol, propanol, isopropanol, butanol, isobutanol, pentanol, hexanol, octanol, decanol, dodecanol, tetradecanol and hexadecanol. Preferably we employ a carboxylic acid as the solvent and particularly a $C_2$ to $C_6$ acid, the most preferred acid being acetic acid. In a preferred embodiment, we employ glacial acetic acid.

The presence of the polar protic organic solvent represents a critical aspect of our invention. In the absence of the solvent described above, either no reaction will occur or at best long reaction times are required to provide the desired product. Employing the designated solvent according to the disclosure above provides the acylhydroximyl halide in good yield and at reaction times ranging from about ½ to 3 hours.

Specific examples of acylhydroximyl halides contemplated herein and prepared according to the inventive method include acetylhydroximyl chlorides, acetylhydroximyl bromide, acetylhydroximyl iodide, acetylhydroximyl fluoride, propionylhydroximyl chloride, butanoylhydroximyl chloride, pentanoylhydroximyl chloride, pentanoylhydroximyl bromide, pentanoylhydroximyl iodide, pentanoylhydroximyl fluoride, hexanoylhydroximyl chloride, nonanoylhydroximyl chloride, undecanoylhydroximyl chloride, undecanoylhydroximyl bromide, undecanoylhydroximyl iodide, undecanoylhydroximyl fluoride, tetradecanoylhydroximyl chloride, pentadecanoylhydroximyl chloride, pentadecanoylhydroximyl bromide, pentadecanoylhydroximyl iodide, pentadecanoylhydroximyl fluoride, heptadecanoylhydroximyl chloride, and eicosanoylhydroximyl chloride.

An additional benefit derived from employing a carboxylic acid or alcohol as the reaction solvent is that the recovery of the acylhydroximyl halide is facilitated and obviates the need for extensive purification procedures, such as a plurality of extractions and recrystallizations. At the completion of the reaction, the product is essentially the desired acylhydroximyl halide and recovery of the same easily proceeds by cooling the reaction mixture to below about 30° C. and lower, suitably 0° to 10° C., whereupon the acylhydroximyl halide crystallizes and is easily separated by filtration from the reaction system or by evaporation of the reaction mixture at about 60° to 90° C. and at low pressures, for example 0 to 40 mm. Hg., whereupon the residue will be substantially pure acylhydroximyl halide. Another means for recovering the product is by diluting the reaction mixture with water at about room temperature thereby precipitating the product. Any by-products formed in the course of the reaction, such as amides, are soluble in the solvent and procedures involving separation by crystallization or precipitation provide the product in a substantially pure form.

The acylhydroximyl halides prepared according to this invention correspond to the formula:

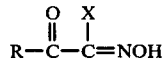

where R is as defined above, where X is Cl, Br, I or F. The novel acylhydroximyl halides provided herein are highly stable compounds with an observed shelf life of over two years. Further, the acylhydroximyl halides were unexpectedly found to be extremely stable even under strong hydrolytic conditions, as for example under the conditions described for their preparation or isolation with added water. Formation of hydroxylamines indicative of hydroxylsis has not been observed. In contrast, such seemingly analogous compounds as aldoximes (RCH=NOH) or halogenated oximes (RCCl=NOH) or hydroxamic acids (RCO=NHOH) are easily hydrolyzed to aldehydes, acids and hydroxylamine hydrochlorides. Further the compounds are useful as a halogenating agent for catalysts, such as platinum on alumina catalysts, as additives to lubricants and greases and as intermediates for the preparation of acids and amides.

In order to more fully illustrate the nature of our invention and the manner of practicing the same, the following examples are presented.

EXAMPLE I

To a solution composed of 250 milliliters of concentrated HCl (7.1 moles) in 750 milliliters of acetic acid (13 moles) heated to 95° C., there was introduced 100 grams of 1-nitro-2-hexadecanone (0.35 mole). The resulting clear solution was maintained at 95° to 104° C. for 100 minutes. The mixture was thereafter allowed to cool to about 25° C. and crystallized solids weighing 75.5 grams after drying were recovered. The filtrate was further cooled to 0° C. and 1 hour and a second crop of crystallized solids weighing 14.2 grams were collected. Thereafter the filtrate was poured into 150 milliliters of water and a third crop of crystallized product weighing 9.68 grams was collected. A combined yield of 94 percent of theoretical was recovered and the product was identified as n-pentadecanoylhydroximyl chloride by infrared, proton nuclear magnetic resonance and elemental analysis.

EXAMPLE II

To 125 milliliters of concentrated HCl there was introduced twelve grams (0.042 mole) of 1-nitro-2-hexadecanone and the mixture was stirred for 24 hours at 105° C. The solids were subsequently recovered by filtration and the residue (11.74 grams) was determined by infrared analysis to be predominantly the charged nitroketone along with a small amount of an amide.

EXAMPLE III

To a 25 milliliter solution composed of 15 parts by weight of concentrated HCl (0.15 mole) in 85 parts by weight of acetic acid (1.42 mole) maintained at 90° C., there was introduced 2.0 grams of 1-nitro-2-hexadecanone (0.00737 mole). The resulting clear solution was maintained at 90° C. for 1 hour and thereafter cooled to 0° C. on an ice bath. Crystallized solids were collected by filtration and weighed 1.44 gram. 25 milliliters of water was added to the filtrate and a second crop of crystals weighing 0.39 gram was collected. The yield of product was 81 percent of theory and was identified as n-pentadecanoylhydroximyl chloride.

EXAMPLE IV

A mixture of 36 parts of concentrated HCl (0.36 mole), 600 parts of acetic acid (10 moles) and 12 parts of 1-nitro-2-hexadecanone (0.042 mole) was maintained at 90° C. for 40 minutes. The resulting solution was poured on to 900 grams of crushed ice and the mixture filtered at 4° C. The recovered crystallized solid weighing 14.33 gram was thereafter recrystallized from hexane and the pure material, n-pentadecanoylhydroximyl chloride, was found to have a melting point of from 69 to 71° C.

EXAMPLE V

A solution of 2.00 grams (0.007 mole) of 1-nitro-2-octadecanone, 1 -milliliter of concentrated HCl and 100 milliliters of acetic acid was heated at 90°-95° C. After diluting with 200 milliliters of water, the precipitate which formed was filtered, water washed, dried and identified as containing n-heptadecanoylhydroximyl chloride.

EXAMPLE VI

A solution of 2.00 grams of 1-nitro-2-hexadecanone, 1.0 milliliter of concentrated HCl and 100 milliliters of propionic acid was heated at 135° C. for 12 hours. After cooling, the filtrate was diluted with about 250 milliliters of water, the solids recovered by filtration, water washed and dried. The residue 1.60 gram was determined by infrared analysis to be a mixture of the charged nitroketone and an amide.

EXAMPLE VII

To a solution of 12.0 grams (0.042 mole) of 1-nitro-2-hexadecanone in 200 milliliters of n-propanol there is added 36 grams (0.36 mole) of 37 percent HCl. The solution temperature is slowly raised to 90° C. over a period of three hours and maintained for five hours. After vacuum evaporating the solution to a volume of 80 milliliters, the residue upon standing crystallizes providing 6.6 grams (52 percent yield) of n-pentadecanoylhydroximyl chloride.

We claim:

1. An acylhydroximyl halide corresponding to the formula:

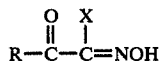

where R is an alkyl group of 3 to 50 carbons and where X is Cl, Br, I or F prepared by contacting a nitroketone with a halogen acid in the presence of a polar protic organic solvent selected from the group consisting of alkanoic acids of up to 16 carbon atoms and alkanols having from 2-16 carbon atoms.

2. An acylhydroximyl halide according to claim 1 where R is from 3 to 40 carbons.

3. An acylhydroximyl halide corresponding to the formula:

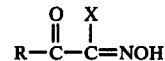

where R is an alkyl group of from 5 to 30 carbons and where X is Cl, Br, I or F.

4. An acylhydroximyl halide according to claim 3 where X is Cl.
5. An acylhydroximyl halide according to claim 3 where X is Br.
6. An acylhydroximyl halide according to claim 3 where X is I.
7. An acylhydroximyl halide according to claim 3 where X is F.
8. n-Pentadecanoylhydroximyl chloride.
9. n-Heptadecanoylhydroximyl chloride.
10. n-Pentadecanoylhydroximyl bromide.
11. n-Pentadecanoylhydroximyl iodide.
12. n-Pentadecanoylhydroximyl fluoride.

* * * * *